(12) United States Patent
Lawrence-Brown et al.

(10) Patent No.: US 7,108,715 B2
(45) Date of Patent: Sep. 19, 2006

(54) ENDOLUMINAL GRAFT

(75) Inventors: Michael Lawrence-Brown, Western Australia (AU); Kurt Liffman, Victoria (AU); David Ernest Hartley, Western Australia (AU)

(73) Assignees: Cook Incorporated, Bloomington, IN (US); William A. Cook Australia Pty Ltd., Queensland (AU)

( * ) Notice: Subject to any disclaimer, the term of this patent is extended or adjusted under 35 U.S.C. 154(b) by 423 days.

(21) Appl. No.: 10/279,446

(22) Filed: Oct. 24, 2002

(65) Prior Publication Data

US 2003/0093145 A1  May 15, 2003

(51) Int. Cl.
*A61F 2/06* (2006.01)

(52) U.S. Cl. .................... 623/1.21; 623/1.25

(58) Field of Classification Search ....... 623/1.25–1.27
See application file for complete search history.

(56) References Cited

U.S. PATENT DOCUMENTS

| | | | | |
|---|---|---|---|---|
| 5,156,620 | A | * 10/1992 | Pigott | 623/1.25 |
| 5,871,537 | A | 2/1999 | Holman et al. | |
| 6,007,575 | A | 12/1999 | Samuels | |
| 6,312,462 | B1 | * 11/2001 | McDermott et al. | 623/1.25 |
| 6,319,276 | B1 | * 11/2001 | Holman et al. | 623/1.11 |
| 6,706,064 | B1 | * 3/2004 | Anson | 623/1.25 |
| 6,827,735 | B1 | * 12/2004 | Greenberg | 623/1.25 |
| 2003/0120331 | A1 | * 6/2003 | Chobotov et al. | 623/1.13 |
| 2003/0225453 | A1 | * 12/2003 | Murch | 623/1.21 |
| 2005/0131515 | A1 | * 6/2005 | Cully et al. | 623/1.13 |

FOREIGN PATENT DOCUMENTS

| | | | | |
|---|---|---|---|---|
| EP | 0521573 | | 1/1993 | |
| EP | 0617930 | | 10/1994 | |
| GB | WO 00/51522 | * | 9/2000 | 623/1.25 |
| WO | 0166038 | | 9/2001 | |
| WO | 2102282 | | 12/2002 | |

OTHER PUBLICATIONS

T.F. Browne et al.; Endovascular and Surgical Techniques; Eur J Vasc Endovasc Surg; vol. 18, pp. 445-449; Article No. Ejvs.1999.0924; 1999.

* cited by examiner

*Primary Examiner*—Suzette J-J Gherbi
(74) *Attorney, Agent, or Firm*—Richard J. Godlewski (57) ABSTRACT

A graft (1) which is in the form of an inflatable member adapted to be formed into a predetermined and/or selected shape when deployed in situ by filling with a filler material (6) which can be made rigid in situ and deployed on a balloon catheter (12). The deployment balloon (13) is formed from a non-compliant material.

12 Claims, 13 Drawing Sheets

ENDOLUMINAL GRAFT

CROSS-REFERENCE TO RELATED APPLICATIONS

This application claims priority of Australian Provisional Application Ser. No. PR 8472 filed Oct. 26, 2001.

TECHNICAL FIELD

This invention relates to a medical device and in particular to an endoluminal graft.

BACKGROUND OF THE INVENTION

Abdominal aortic aneurysms and problems in other body lumens have been treated by the use of stent grafts or prostheses of a variety of constructions, but due to their essentially rigid construction, even in a collapsed state, there are problems inserting such grafts into an aorta or other body lumen.

SUMMARY OF THE INVENTION

It is the object of this invention to provide a graft, which is of a minimal size for insertion, but can carry out essentially the same function as existing stent grafts.

Also, when treating occlusive disease in arteries, it is desirable to have a delivery system, which is as small as possible during delivery, but can be expanded in situ to a selected size to treat the occlusive disease.

With imaging techniques using Magnetic Resonance Imaging (MRI), it is desirable to have grafts, which do not include metallic stents as these cause flaring with MRI. It is a further object of this invention to provide such a grafting system.

In one form therefore the invention is said to reside in a graft for maintenance or repair of a lumen of the body, the graft including an inflatable member having a selected inflated shape when deployed in situ by filling with a settable or filler material which can be set and become rigid in situ.

Preferably the graft is deployed on a deployment balloon, the deployment balloon being formed from a non-compliant material.

In an alternative form, the invention is said to reside in a method of deployment of a graft within a body lumen, the graft being of a type to be formed in its final shape in situ and set into that shape, the method including the steps of:

mounting the graft in a contracted state onto a deployment balloon on a delivery device, inserting the delivery device so that the graft is positioned at the desired position in the body lumen, inflating the deployment balloon to place the graft adjacent the wall of the body lumen, placing a settable or filler material that can be set into the graft to form the graft into its desired final shape, setting the graft into its final shape by rigidising the settable or filler material, as hereinafter defined, deflating the deployment balloon, and removing the delivery device.

Preferably the deployment balloon is formed from a non-compliant material as hereinafter defined.

Throughout this specification the term "non-compliant", with respect to the balloon, is intended to mean that the balloon is constructed from a material, which at normal intended inflation pressures, is essentially non-elastic, whereby upon inflation, a selected size and shape of balloon is provided. The use of such a non-compliant balloon as the deployment balloon will help to ensure that a finally placed graft has a lumen of a selected size and shape.

Throughout this specification the term "non-compliant or semi-compliant", with respect to the graft material, is intended to mean that the graft is constructed from a material, which at normal intended inflation pressures, is non elastic or only slightly elastic so that it can conform to the walls of a lumen into which it is placed but will not significantly distort during inflation.

Throughout this specification, the term "rigidised" is intended to mean that the material for inflation or filling of the graft is able to be made more rigid but does not exclude a final form in which the material is flexible.

In a preferred form of the invention, the graft is of a type having an internal lumen, being a lumen that is not open to the body lumen, and the step of setting the graft into its final shape includes the step of inserting a suitable liquid into that internal lumen to thereby inflate it to the predetermined or selected shape.

In one embodiment, the graft is generally of an elongate torroidal or annular shape when in the inflated condition to define a lumen therethrough that provides an artificial flow-path for the body lumen.

The graft can be formed from a double walled plastic tube thereby providing an inner wall and an outer wall and wherein the settable or filler material or inflation material is provided between the inner wall and the outer wall to inflate the graft to form it into its final shape.

Preferably, the graft is evacuated before being inserted into the body lumen so that during inflation there are no air pockets in the final shape when inflated.

The graft has an inflow tube for the supply of settable or filler material to the graft and can also have an outflow tube so that complete filling of the graft can be determined by excess flowing out of the graft through the outflow tube. The inflow and outflow tubes can be connected in use to tubes or associated with the lumens delivery device that extend to outside the body of a patient so that the settable or filler material can be supplied and the excess material flowing out of the graft can be observed.

Webs or baffles can be provided between the inner and outer walls of the graft to ensure that the graft thoroughly inflates to a predetermined or selected shape. The webs or baffles can be provided by joining of the inner and outer walls at intervals or can be provided by webs of material joined to each wall.

The material of construction of the walls of the tube can be any bio compatible film and in a preferred embodiment of the invention, the bio-compatible film is made from a non-compliant or semi-compliant material as hereinbefore discussed so that when inflated, it forms a selected size and does not inflate too much or in a distorted manner but is able to conform to the wall of a vessel.

The liquid which is inserted into the graft to inflate it to the selected shape is preferably a bio-compatible material and can be a monomer, a liquid pre-polymer or an un-crosslinked polymer. The setting or rigidising of the liquid or filler material inserted into the graft can be by polymerisation of the monomer or pre-polymer or by cross-linking of the liquid polymer. The polymerisation can be by irradiation such as with UV, IR or visible light radiation to initiate the polymerisation or cross-linking. Such irradiation can be provided into the lumen by means of a fibre optic cable inserted through a lumen of the delivery device.

Where the polymerisation or rigidising is achieved by the use of radiation such as UV, IR or visible radiation and the graft is formed from a double walled plastic tube thereby providing an inner wall and an outer wall, the outer wall is preferably a radiation opaque material and its inner wall is a radiation transparent material.

The graft can have on its outer surface at one or both ends one or more blood flow prevention rings or sealing ridges or flanges circumferentially around each end. These can be provided so that once in place, flow of blood cannot go outside the graft. The ridges, flanges or rings can also assist with prevention of longitudinal movement of the graft within the body lumen under the influence of, for instance, blood flow.

The graft can be fenestrated or bifurcated as required for particular applications.

There can be means provided to enable detachment of the tubes through which the setting or filler material is supplied to the graft and excess material removed before deflation of the deployment balloon. Such a detachment means can utilise a fusible or separable link, a severing mechanism or some other arrangement.

In a preferred embodiment of the invention, the inflation pressure of the graft's settable or filler material can be selected to be slightly higher than the inflation pressure of the deployment balloon. For instance, the deployment balloon can be inflated at perhaps five atmospheres and the graft inflated with the settable material at 8 to 10 atmospheres. By this arrangement, thin or thick spots in the wall of the graft can be avoided.

A delivery device for deployment of the graft according to this invention can be a multi-lumen catheter. Lumens can be provided for a guide wire, inflation material such as brine for the deployment balloon, supply and return lumens for the settable or filler material for the graft and a lumen for the fibre-optic cable for the setting stage.

Alternatively, tubes for the supply and optionally return of settable or filler material can be provided external to the delivery catheter.

Preferably, the multi-lumen catheter of the delivery device includes a soft conical distal tip, an annular recess along the body of the delivery device into which the deployment balloon and graft is inserted and a sheath which is adapted for covering the deployment balloon region during initial insertion.

In a further form, the invention can be said to reside in a deployment device for an inflatable graft, the deployment device having a delivery catheter, an inflatable balloon at or near the distal end of the delivery catheter, the catheter having at least a guide wire lumen and a lumen to supply inflation fluid for the balloon, a tube to supply settable or filler material extending from a proximal end of the delivery catheter to an inflatable graft mounted on to the balloon.

Preferably the balloon is formed from a non-compliant material.

Preferably, the delivery catheter is a balloon catheter.

Preferably, the delivery catheter, the balloon, the tube and the graft are covered by a sleeve coaxial with the balloon catheter.

There can be further included a second tube extending along the delivery catheter from the graft so that excess settable or filler material can be carried away from the graft.

There can be further included a lumen in the delivery catheter to extend a fibre optic cable to the graft to provide radiation to set the settable or filler material in the graft.

There can be further included means to enable detachment of the tubes through which the setting material is supplied to the graft. The means to enable detachment of the tubes can utilize a fusible or separable link or a severing mechanism.

Hence, according to one embodiment of this invention, it is proposed that the graft be a synthetic material tube where the walls of the tube contain a ribbed or webbed inner cavity that runs the length of the graft. The graft has little structural strength and, by itself, cannot act as a channel for the blood flowing through the AAA. However, when the cavity wall of the graft is filled with radiation-activated liquid polymer, the graft will obtain the appropriate structural strength (and flexibility) once the system has been exposed to suitable radiation.

Due to the drag force of blood flowing through the graft, it is preferable that it has some means of keeping itself in place within the lumen. For this purpose, external counter-flow ridges can be built into the outer wall of the graft.

The graft is preferably delivered to the body lumen via a balloon catheter surrounded by a restraining sleeve. The graft, in a collapsed/compressed state, surrounds the balloon while the graft is being delivered to the aneurysm via an easily accessible, remote artery. Once the tube is in the optimal position, the sleeve is withdrawn, the balloon is expanded and the tube is filled with the polymer via a separate delivery tube. When the cavity wall is filled with the polymer, a UV or light source is introduced via an optical fibre. Appropriate exposure to the light causes the polymer to set. The polymer and the containment graft will now have obtained the required rigidity. The balloon is subsequently deflated and the catheter withdrawn. Finally the UV polymer inlet tube is cut and the graft is secured in place by the strategically placed "counter-flow" ridges, which imbed themselves into the arterial wall.

The example of a graft in the form of a simple tube has been used to illustrate the concept, however, the graft can have a more complex structure. For example, it can have the shape of a bifurcated endoluminal graft, i.e., a single tube that bifurcates into two tubes. The graft can also have this shape or indeed another shape where any number of tubes are joined together in a manner that is appropriate for the physiology of the patient and/or the desired medical application.

In other embodiments, there can be more than one internal lumen and there can be more than one type of settable or filler material for the different internal lumens or the settable or filler material can be supplied to the different lumens at different pressures. Alternatively, a first internal lumen can be inflated with settable material and rigidised and then a further internal lumen inflated with settable material and rigidised.

Current endoluminal grafts can also have fenestration holes or tubes in the wall of the graft. These holes or tubes act as entrance points for separate tubes, often referred to as extension legs. The graft of the present invention can also be adapted to this practice.

BRIEF DESCRIPTION OF THE DRAWING

This then generally describes the invention but to assist with understanding, reference will now be made to preferred embodiments of the invention. In the drawings.

DETAILED DESCRIPTION

Figure 1:
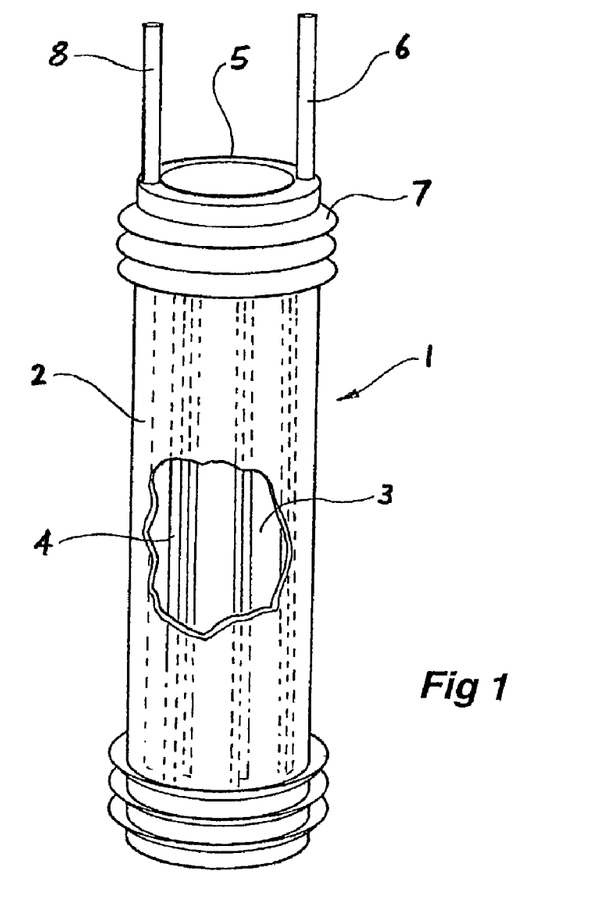
FIG. 1 shows a schematic view of a graft of one embodiment of the invention.
Figure 2:
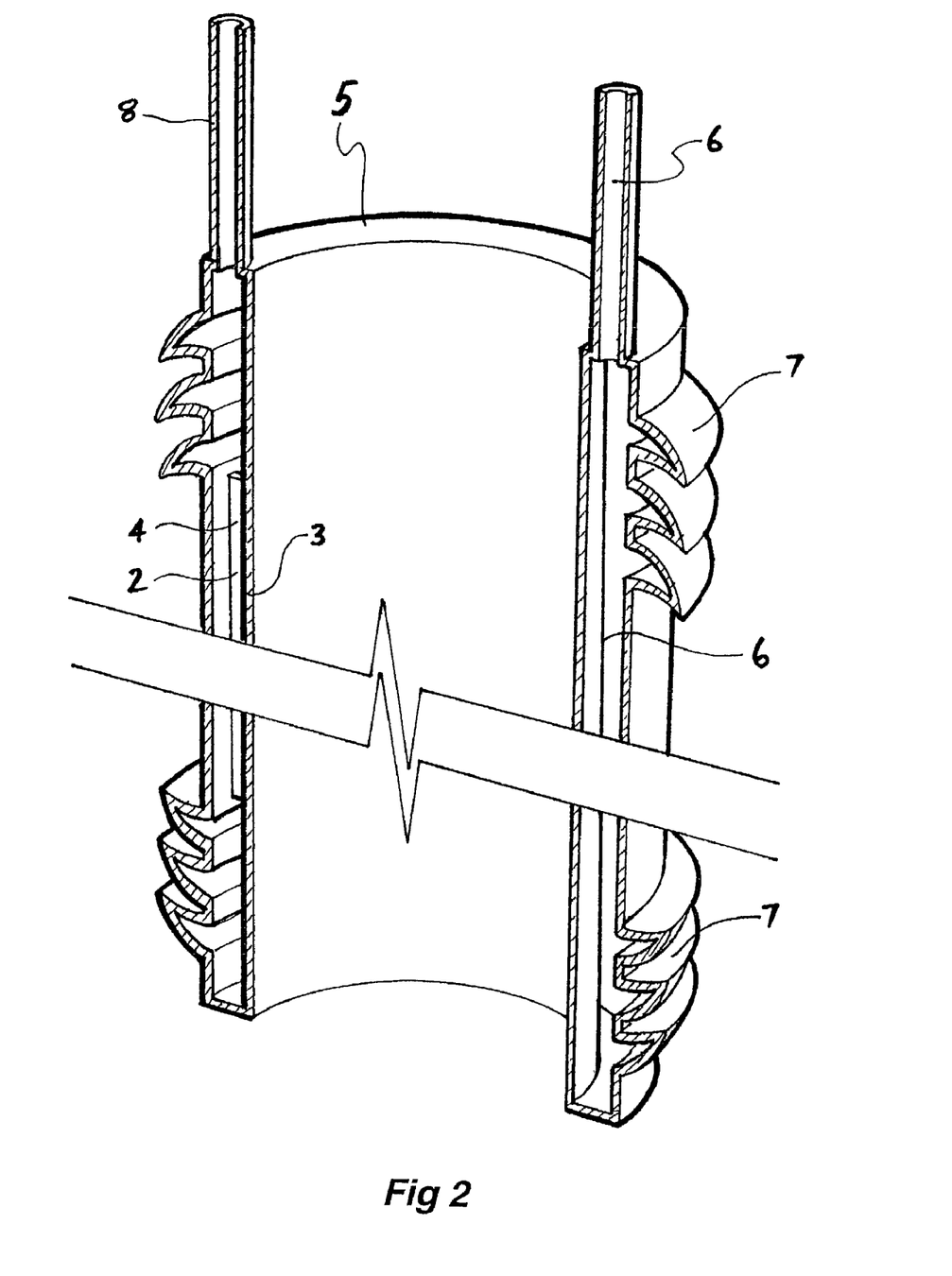
FIG. 2 shows an enlarged longitudinal cross sectional view of the graft of FIG. 1.
Figure 3:
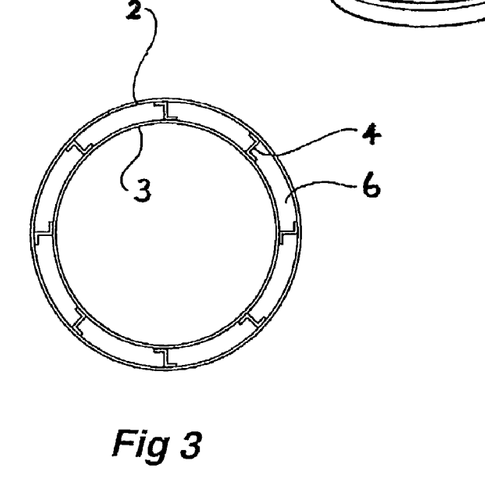
FIG. 3 a schematic view of a graft of FIG. 1 in cross section.

Now looking more closely at the drawings and, in particular, FIGS. 1 to 3 which show a first embodiment of the graft according to this invention, it will be seen that the graft comprises an annular tubular hollow body 1, which is formed from an outer wall 2 and an inner wall 3. Between the inner and outer walls are webs 4, which do not extend the full length of the graft. The annular hollow body has an end wall 5 between the inner wall 3 and the outer wall 2. The walls 2, 3 and 5 define a hollow space 6 into which can be inserted a settable or filler material under slight pressure to inflate the graft to a predetermined or selected tubular shape as shown in FIG. 1 and then after setting of the settable or filler material, the graft remains in that shape. The graft has an inflow tube 6 at one end through which can be supplied the settable or filler material. There is also a further return or outflow tube 8 for return of excess settable or filler material. The outflow tube 8 could extend from the opposite side of the graft 1 as inflow tube 6 The return or outflow tube 8 could also extend from the opposite end of the graft 1 and extend back through the annular opening and co-extend along with inflow tube 6 to assure that settable or filler material has been caused to flow completely through the graft for thorough inflation.

It is preferred that the graft, when in its deflated state, is evacuated so that no air is inside the graft when it is inserted into a lumen of a body.

At each end of the graft are a series of annular flanges or ridges 7 which are in effect continuations of the outer wall 2 and when the body is inflated with the settable or filler material, the annular flanges or ridges 7 are also inflated. In use these annular flanges, when inflated, engage against the walls of the body lumen to provide a seal so that blood flow will not occur on the outside of the graft. These flanges or ridges help to ensure that the drag force from the blood flowing through the graft does not displace the graft from its optimal position.

In FIG. 2 showing a longitudinal cross section of the UV graft, it can be seen that an approximately 5 mm thick cavity exists in the wall of the tubular graft and, when inflated, the total internal width of the inner tube of the graft is in the range of 10 to 20 mm. The internal structure of the stability flanges or ridges 7 is also shown at either end of the graft.

The cavity 6 within the graft has a webbed or a ribbed internal structure. The webs or ribs 4 are designed to limit the expansion of the cavity during the polymer injection phase. This ensures that the UV graft does not balloon at points where the external wall of the graft is not constrained by an arterial wall or by laminated thrombus. The ribs can have a non-continuous longitudinal or helical shape. Gaps in the longitudinal or helical structure allow the settable or filler material such as a UV polymer to flow freely through the entire cavity. The ribs 4 do not necessarily extend to the ends of the graft. Of course, other rib shapes are possible.

It will be realized that the graft, as shown in FIGS. 1 to 3, can have a different shape than an essentially cylindrical shape depending upon the form of the lumen into which the graft is to be supplied. For instance, the graft can have an arcuate shape if it is to be placed in a spot such as the thoracic arch or can have constrictions in diameter if it is to be placed, for instance, in the aorta and extend down one of the iliac arteries. As well be discussed with further embodiments, the graft can have apertures or bifurcations.

The graft of the present invention is preferably made from a bio compatible plastics material that is transparent to UV and/or visible light and non-compliant to stretch. As discussed above, the outer layer of the bio compatible plastics material can be opaque to UV and/or visible light.

FIGS. 4 to 7 show the various stages of deployment of a graft according to this invention into a body lumen.

Figure 4:
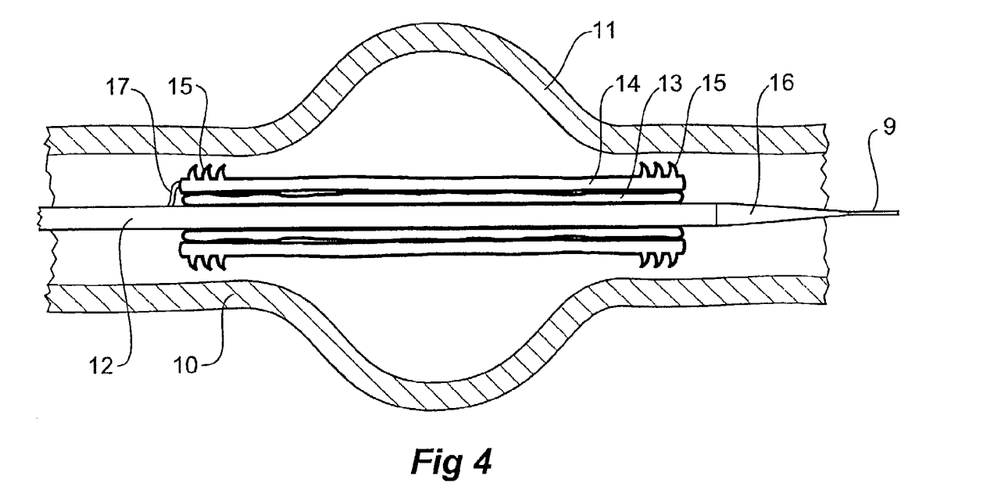
FIG. 4 shows the first stage of a deployment procedure for a graft of one embodiment of the present invention in an abdominal aortic aneurysm.

In this case, the body lumen is an aorta 10 with an aneurysm 11. The deployment device 12 such as a catheter with a deployment balloon 13 and the graft 14 mounted onto it is introduced on a guide wire 9. Introduction by the deployment device including a tapered tip 16 to assist with introduction into the aorta.

Figure 5:
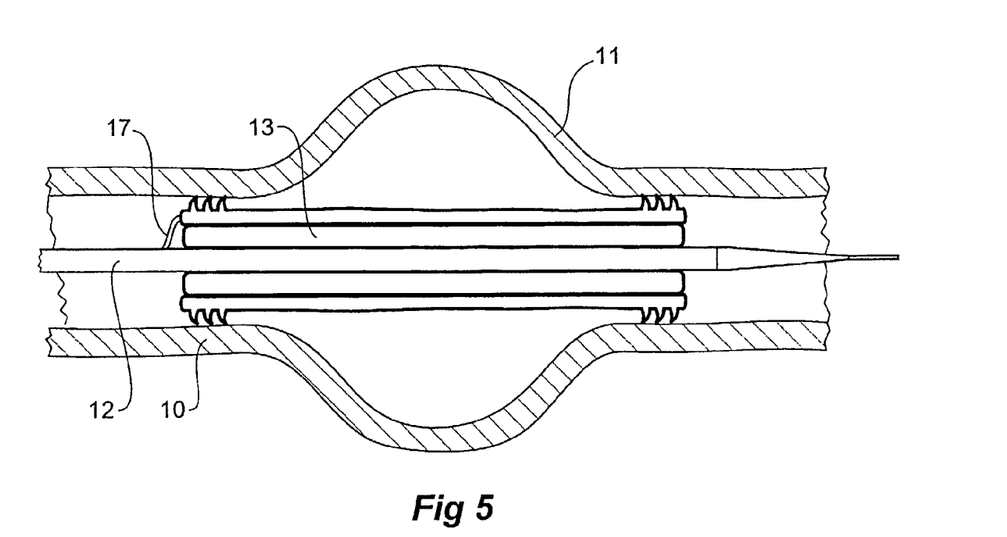
FIG. 5 shows a second stage of a deployment.
Figure 6:
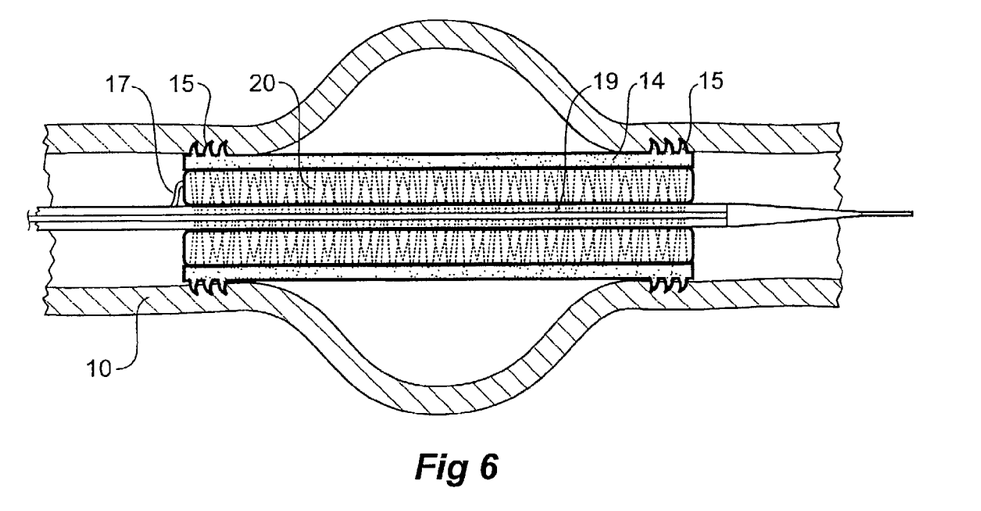
FIG. 6 shows a third stage of a deployment procedure.

Once the graft is in the correct position, as ascertained by MRI or X-ray fluoroscopy or some other visualization technique, the balloon 13 is inflated as shown in FIG. 5. The balloon 13 is manufactured from a non-compliant material. This means that the balloon will expand to a predetermined and/or selected size and shape but not go beyond that shape under normal inflation. Expansion continues until the uninflated graft 14 has engaged the walls of the aorta 10 beyond the aneurysmal region 11.

The balloon 13 is then held inflated and settable or filler material is then inserted into the graft 14 until it, too, is inflated, and the sealing flanges or ridges 15 at each end of the graft 14 engage into the walls of the aorta 10 to engage the graft within the aorta. Preferably, the pressure of the settable or filler material in the graft 14 is slightly greater than the pressure in the balloon 13 so that the balloon does not distort the final shape of the graft 14. Settable or filler material is supplied to the graft 14 by means of inflow tube 17.

After the tube has been filled, a fibre optic cable 19, which is either present in the delivery device or is inserted through the delivery device 12, is used and UV radiation 20 is supplied in the region of the graft 14 to set the settable or filler material in the graft. See FIG. 6.

Figure 7:
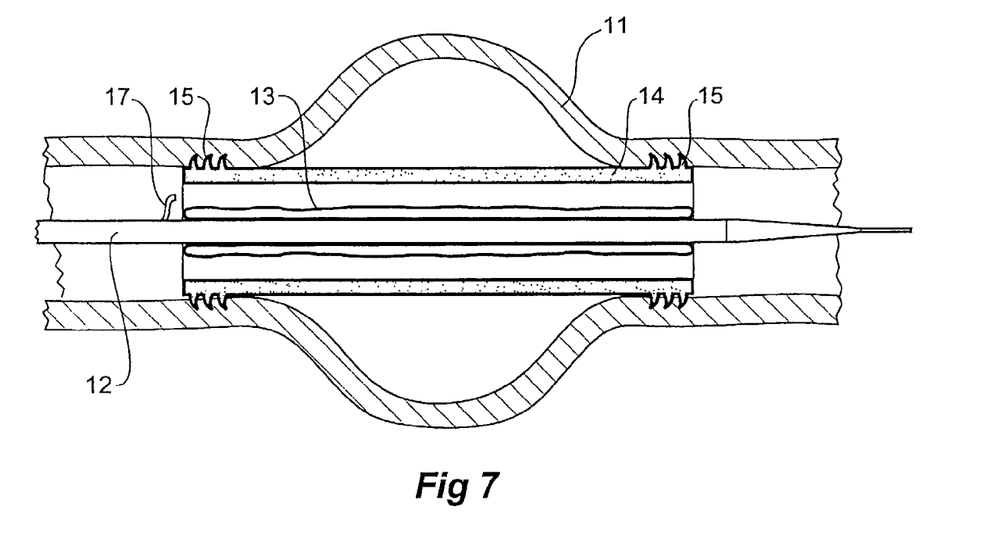
FIG. 7 shows a final stage of a deployment procedure.
Figure 8:
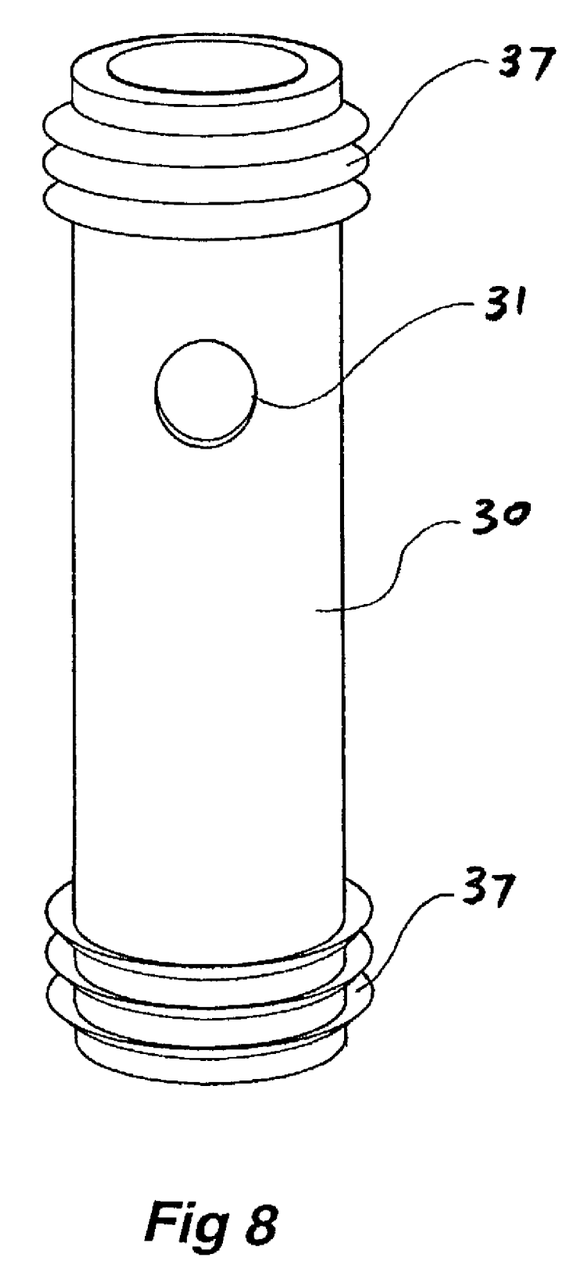
FIG. 8 shows an alternative embodiment of a graft of the present invention.

After the settable or filler material has set in both the graft and the delivery tube 17, a mechanical means or other means (not shown) is used to separate the tube 17 from the graft 14 and the balloon 13 is deflated as shown in FIG. 7. The delivery device 12 can then be removed to leave the graft 14 in place bridging the aortic aneurysm 11.

FIGS. 8 to 11 show the use of the graft of the present invention as a fenestrated graft and how a side arm is inserted through such a fenestration. The graft 30 has at least one fenestration or aperture 31 along its length. The fenestration is designed to enable a side arm to extend through the fenestration into a branch of the body lumen such as occurs where the renal arteries leave the aorta.

Figure 9:
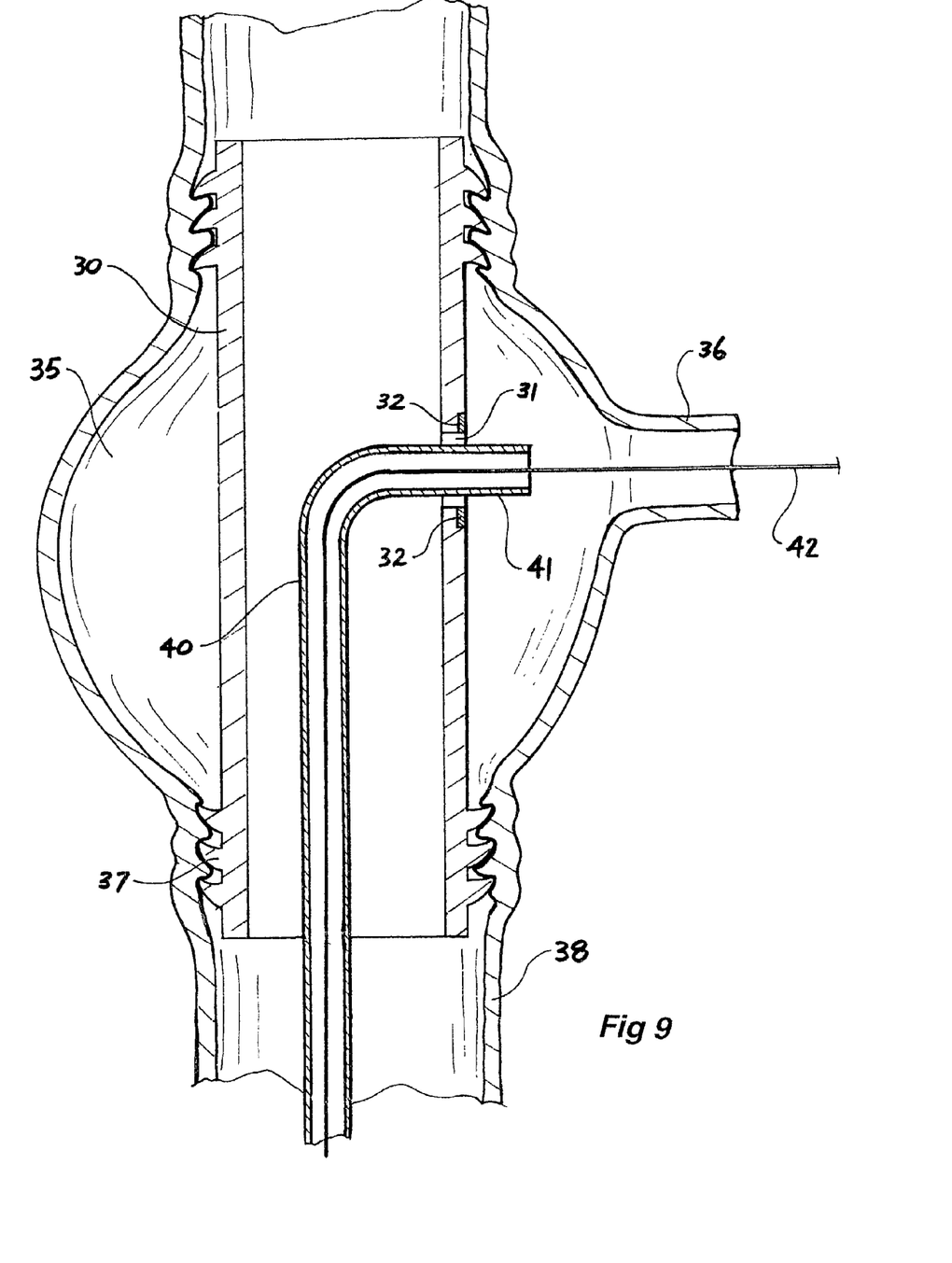
FIG. 9 shows an alternative embodiment of a graft of the present invention and the process of delivering an extension to a branch artery via a guide wire threaded through a fenestrated graft.

As can be seen in FIG. 9, an aneurysm 35 has occurred in an aorta and the renal artery 36 is incorporated in the aneurysm. In such a situation, the graft is placed so that it extends across the aneurysm and the sealing flanges or ridges 37 engage into non-aneurismal material of the aorta 38. Placement can be by the method discussed with respect to FIGS. 4 to 7.

The graft 30 is designed so that once installed, the fenestration 31 is immediately opposite the renal artery. Suitable radiopaque markers 32 such as gold or MRI opaque markers can be used to confirm the positioning of the fenestration. As shown in FIG. 9, a catheter 40 with a cranked portion 41 at its end is used to place a guide wire 42 extending into the renal artery 36.

An arrangement, as shown in FIGS. 4 to 7, can be used to insert a branch graft through the fenestration 31.

Figure 10A:
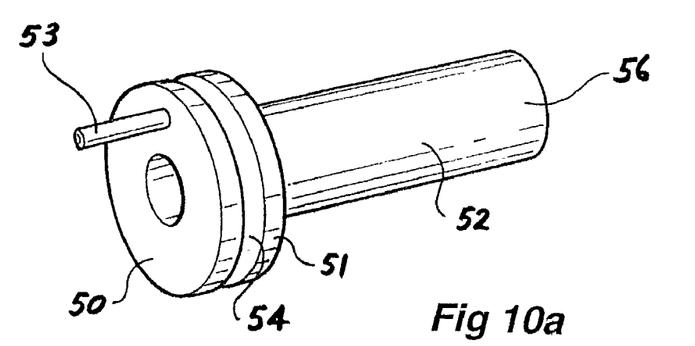
FIGS. 10A and B show an embodiment of a double flange extension leg graft for connecting a fenestrated graft to a branch artery of the type as shown in FIG. 8 or 9.
Figure 10B:
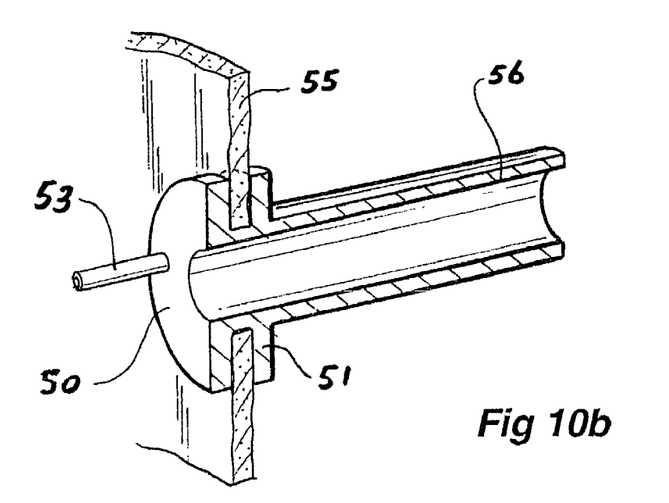

One embodiment of the branch graft is shown in FIG. 10A and the installation of the branch graft is shown in FIG. 10B. The graft has a pair of flanges 50 and 51 at one end of an elongate body 52. A tube 53 is used for insertion of the settable or filler material.

In use, the branched graft is positioned that when inflated, the gap 54 between the flange 50 and the flange 51 fits around the fenestration 31 in the wall 55 of the graft 30. The end 56 of the branch graft can have sealing ridges (not shown) which are used for sealing into the branch artery.

Figure 11:
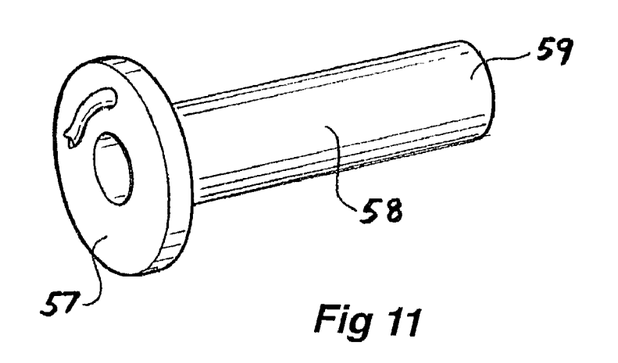
FIG. 11 shows an embodiment of a single flange extension leg graft of the present invention.

FIG. 11 shows an alternative embodiment of a branch graft. Due to variations in vascular anatomy, it is sometimes impossible to have a flange on the outside of the main fenestrated graft. For example, if the primary graft is in contact with the main artery wall, there can be no room to expand a flange on the outside of the graft. In such circumstances, a single flange graft as shown in FIG. 11 can be used where the flange 57 resides inside the primary graft tube and the body 58 is passed through the fenestration 51 before being inflated. Once again, the terminal end 59 can have one or more sealing flanges or ridges.

In some situations, an aortic aneurysm occurs in the region of the aorta between the renal arteries and the iliac bifurcation where the aorta divides into two flow paths. Such an aneurysm can be so close to the bifurcation, that it is impossible to place a tubular graft successfully in such situations. To treat this type of aneurysm, it is best to use an endoluminal graft that is similar in shape to the anatomy of this region of the aorta, thus the graft has a bifurcation in it.

Figure 12A:
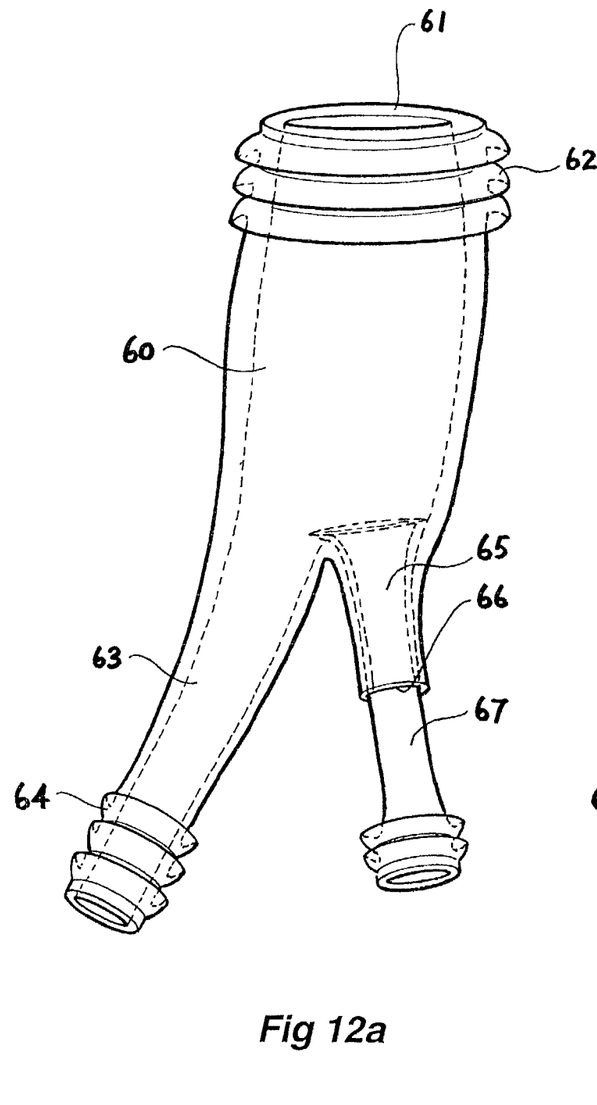
FIGS. 12a and b show an embodiment of a bifurcated graft with an extension leg of the present invention.
Figure 12B:
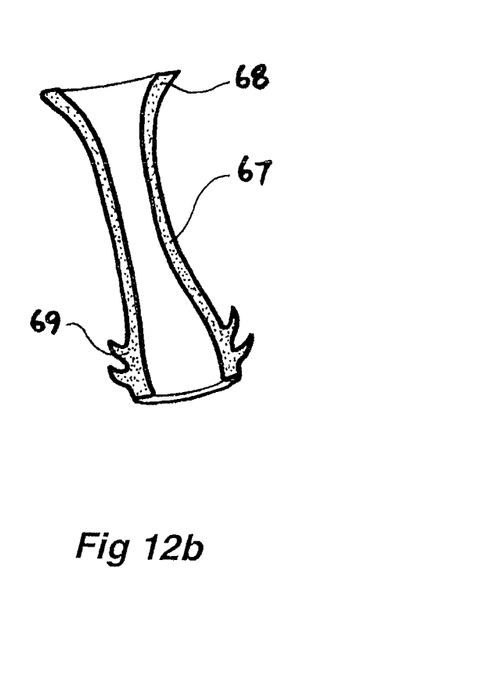

FIGS. 12a and b show an example of a bifurcated graft of the present invention. The bifurcated graft comes in two parts. A primary section 60 has a larger upper body portion 61 with sealing flanges or ridges 62 and a tapered lower portion 63 with sealing flanges or ridges 64 adapted in use to seal into one of the iliac arteries. A short leg 65 terminating in an aperture 66 is provided between the ends of the graft. Into this short leg 65 can be inserted an extension leg graft 67 which is shown in cross section in FIG. 12B. Once the main graft 60 has been placed, inflated and set, then the extension graft 67 is inserted with its upper end 68 within the short leg 65 and sealing flanges or ridges 69 engaging into the other iliac artery to provide a good seal.

Depending upon the topography of the aorta in the region of the aneurysm the extension into the contralateral iliac artery can be by an arrangement of an extension leg of the type discussed above for a renal artery.

FIGS. 13 to 16 show an alternative embodiment of a deployment device and a method of deploying the graft of the present invention. For ease of viewing, the aorta is not shown in this embodiment.

Figure 13:
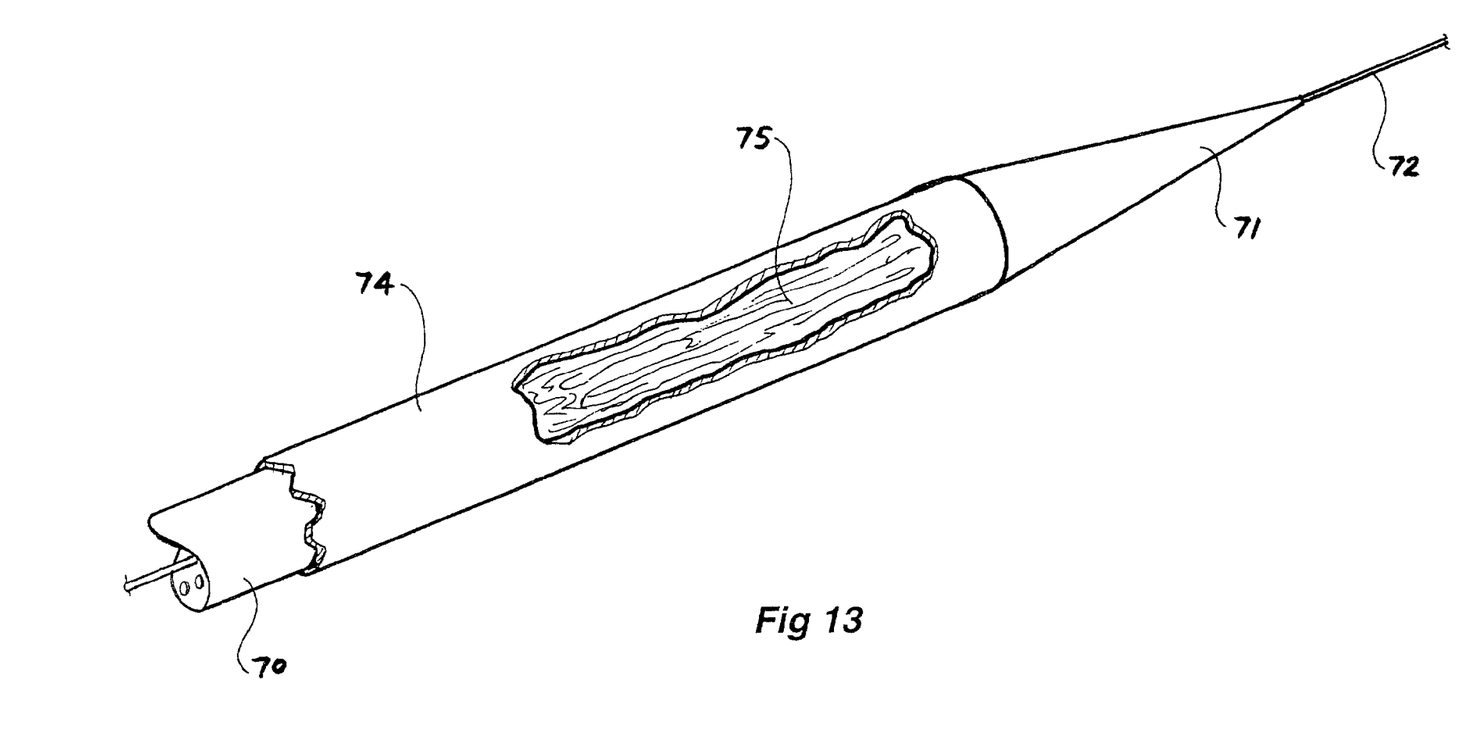
FIG. 13 shows one form of delivery device for a graft of the present invention with the graft mounted thereon in the deflated state with a sheath covering the graft.

In this embodiment the deployment device comprises a catheter 70 which terminates in a tapered front portion 71 and which can be slid over a guide wire 72 and a sheath 74 covers the catheter 70 up as far as the tapered portion 71.

Near the tapered portion 71 of the catheter 70 is an annular region into which is mounted as is shown in the cutaway section of the sheath, a graft of the present invention 75 mounted on a balloon.

Figure 14:
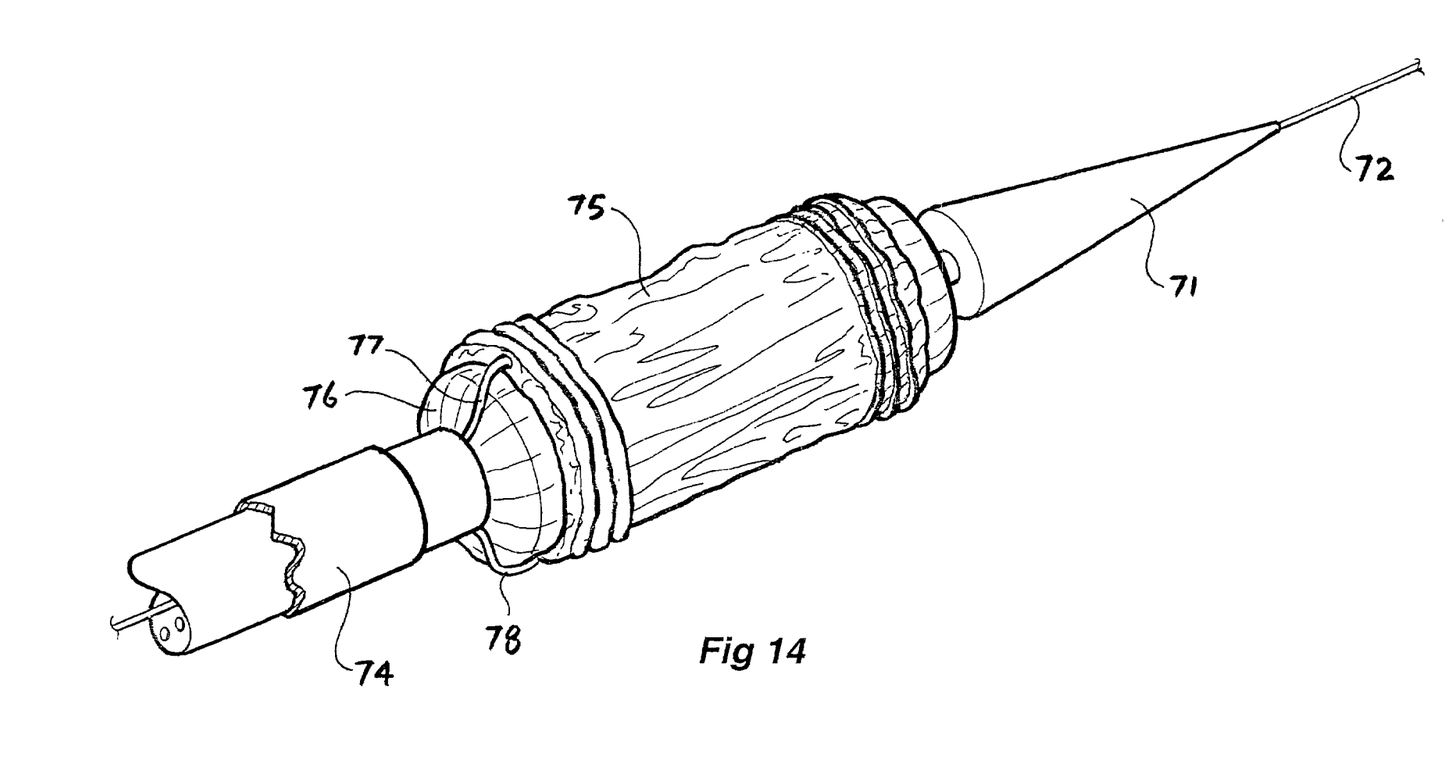
FIG. 14 shows a second stage in the deployment of the embodiment of FIG. 13.

As shown in FIG. 14, the sheath 74 has been withdrawn so that the balloon and graft is now exposed and the balloon 76 has been inflated whilst the graft 75 carried on the balloon 76 remains uninflated with the settable and/or filler material. In this embodiment there are two tubes 77 and 78 leading from the catheter to the inflatable graft.

Figure 15:
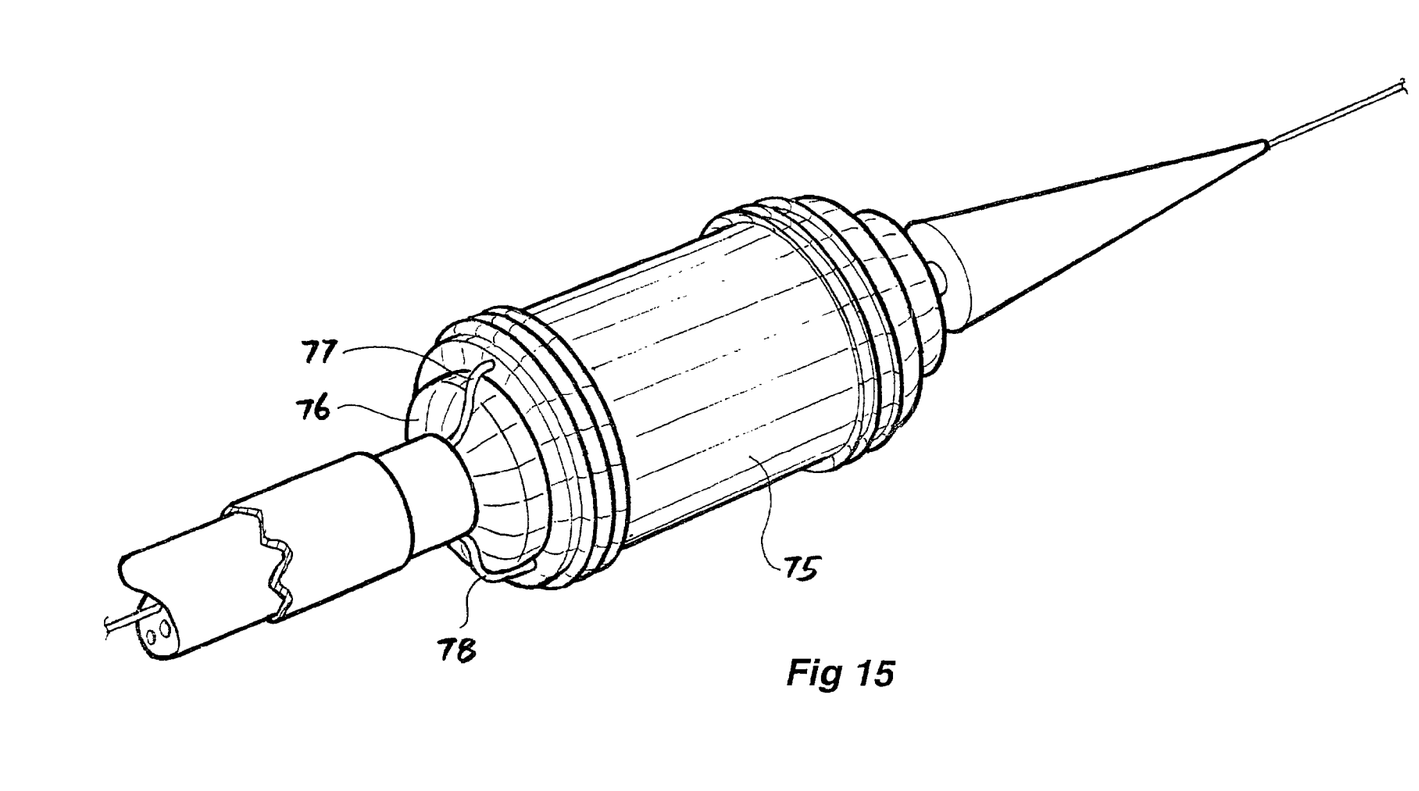
FIG. 15 shows a third stage in the deployment of the embodiment of FIG. 13.

As shown in FIG. 15, settable and/or filler material has been forced into the graft 75 through the inflow tube 77 so that it has expanded while being supported on the balloon 76 and the outflow tube 78 allows for return of excess settable and/or filler material so that it can be ascertained that the graft 75 has been completely inflated with the settable and/or filler material. As discussed earlier, the pressure of settable and/or filler material is higher than the pressure applied to the balloon.

Figure 16:
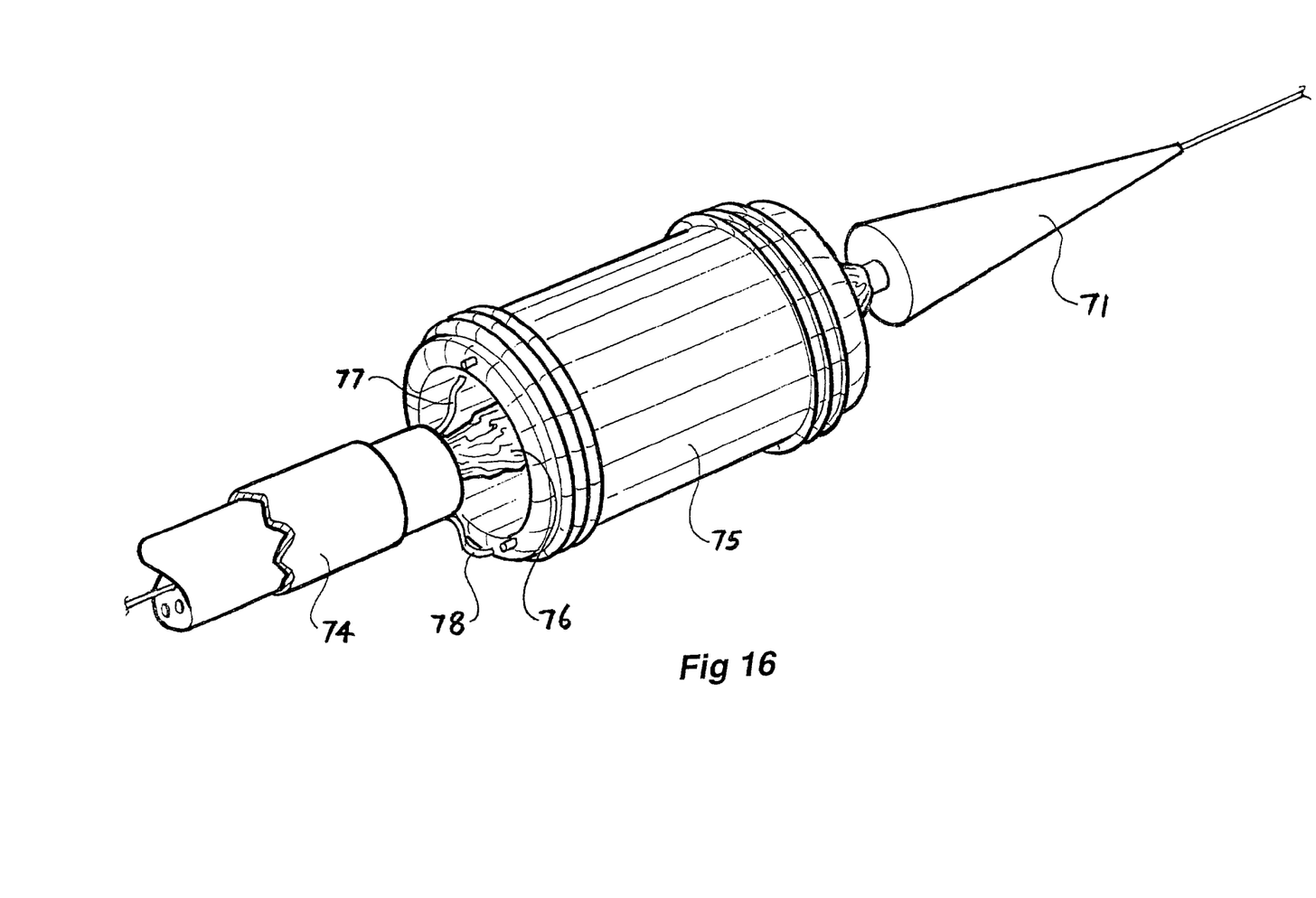
FIG. 16 shows a final stage in the deployment of the embodiment of FIG. 13.

The settable or filler material is then irradiated or by other means set so that it forms a substantially rigid graft and then, as shown in FIG. 16, the inflow and outflow tubes 77 and 78 are disconnected by means not shown and the balloon 76 within the graft 75 is deflated. The sleeve 74 can then be slid forward again so that it covers the balloon and reaches the tapered portion 71 at which stage the entire deployment assembly can be withdrawn leaving the graft in place.

The alternative embodiment shown in FIGS. 17 to 22 shows the use of the present invention with the deployment device in the form of a balloon catheter.

Figure 17:
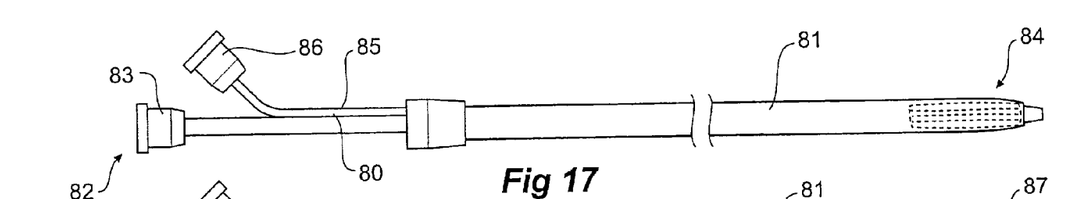
FIG. 17 shows a further embodiment of the delivery device of the present invention in the form of a balloon catheter.

In FIG. 17 it will be seen that the balloon catheter arrangement includes a catheter 80 with a sleeve 81 over it. At the distal end 82 of the catheter 80 is a connection point 83 for a syringe and at the proximal end 84 is a balloon and graft encased by the sheath 81. A tube 85 extends from a fluid supply port 86 to the graft as will be discussed later.

Figure 18:
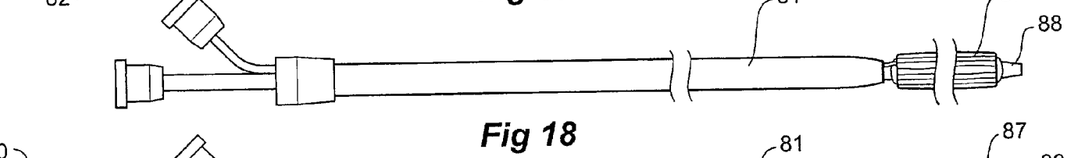
FIG. 18 shows the embodiment of FIG. 17 with the sleeve withdrawn.

As can be seen in FIG. 18, the sleeve 81 has been withdrawn to expose the graft 87 surrounding a balloon 88. Both the graft 87 and balloon 88 are in a deflated condition.

Figures 19, 20:
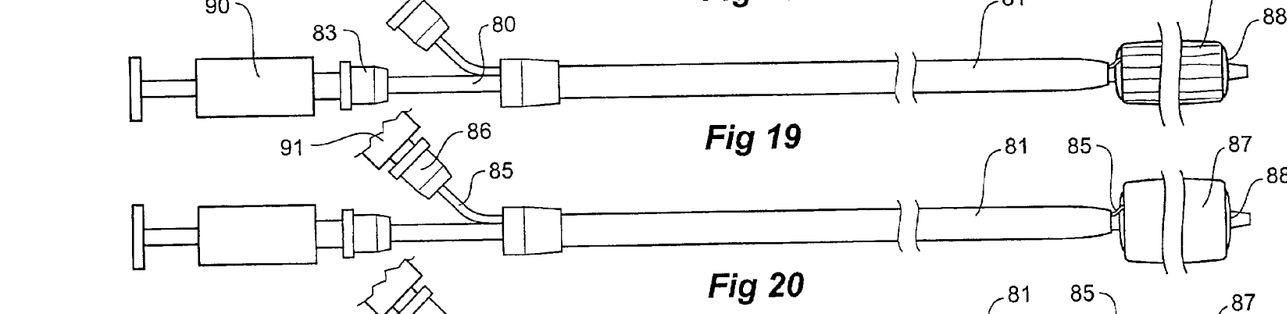
FIG. 19 shows the embodiment of FIG. 18 with the balloon inflated.
FIG. 20 shows the next stage in which the graft is inflated.

Now looking at FIG. 19, it will be noted that a syringe 90 has been connected to the connection point 83 on the catheter 80 and inflation material supplied to the balloon 88 so that this is inflated but the graft 87 on the balloon 88 remains deflated.

In the next stage, settable or filler material supply syringe 91 is connected to the supply port 86 and settable or filler material supplied through the tube 85 to the graft 87 and this is inflated over the inflated balloon 88.

At this stage a fibre optic cable is deployed through the balloon catheter 80 to provide UV or visible light to set the settable or filler material in the graft 87.

Figures 21, 22:
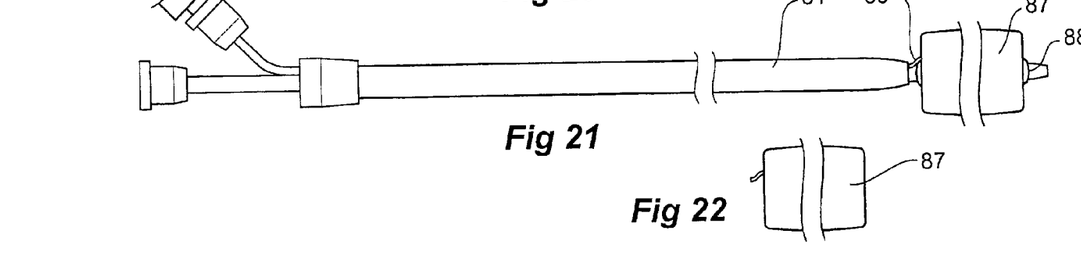
FIG. 21 shows the next stage in which the balloon is deflated.
FIG. 22 shows the final stage in which the delivery device is withdrawn and the graft is left in place.

After the graft 87 has been set, the balloon 88 is deflated as shown in FIG. 21. The tube 85 can then be severed adjacent the graft 87 and then the deployment device can be removed to leave the graft in place as shown in FIG. 22.

A clear advantage of the graft and deployment system of the present invention over the prior art is that the graft can mould itself to the walls of the artery and/or the laminated thrombus. Current systems are unable to do this because the expansion and rigidity of the current grafts are usually dependent on metal stents. These stents cannot deform to fit the small irregularities that can exist in the artery or laminated thrombus. This, in turn, can lead to the formation of endoleaks, repressurization of the aneurysm and, eventually, rupture.

Throughout this specification various indications have been given as to the scope of this invention but the invention is not limited to any one of these but can reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A graft for maintenance or repair of a lumen of the body, the graft comprising an inflatable member having a predetermined inflated shape when deployed in situ by filling with a filler material which can be set and becomes rigid in situ wherein the graft has an internal lumen not open to the body lumen, and into which the filler material is placed and wherein the graft has an inflow tube for the supply of filler material to the graft and an outflow tube so that complete filling of the graft can be determined by excess flowing out of the graft through the outflow tube and wherein the graft includes at least one fenestration in the graft and communicates with a blood flow lumen of the graft.

2. The graft as in claim 1 wherein the graft is generally of an elongate torroidal or annular shape when in the inflated condition and wherein the blood flow lumen provides an artificial flowpath for the body lumen.

3. The graft as in claim 1 wherein the graft is formed from a double walled plastic tube thereby providing an inner wall and an outer wall and wherein the fhler material is provided between the inner wall and the outer wall to inflate the graft into its predetermined inflated shape.

4. The graft as in claim 3 wherein the graft has webs or baffles between the inner and outer walls of the graft to ensure that the graft thoroughly inflates to a selected shape.

5. The graft as in claim 1 wherein the graft is formed from a bio compatible film.

6. The graft as in claim 5 wherein the bio compatible film is a non-compliant material or a semi-compliant material so that when inflated it forms a selected size and does not over inflate or in a distorted manner.

7. The graft as in claim 1 wherein the filler material is a bio-compatible material.

8. The graft as in claim 1 wherein the filler material is selected from the group comprising a monomer, a liquid pre-polymer or an Un-crosslinked polymer.

9. The graft as in claim 1 wherein the filler material is set by exposure to UV, IR or visible light.

10. The graft as in claim 1 wherein the graft has on its outer surface at one or both ends one or more sealing ridges or flanges circumferentially around the end.

11. The graft as in claim 1 wherein the graft includes a bifurcation.

12. The graft of claim 1 wherein the graft further includes a deployment balloon of a non-compliant material.

* * * * *